United States Patent [19]
Chen et al.

[11] Patent Number: 5,997,569
[45] Date of Patent: Dec. 7, 1999

[54] FLEXIBLE AND ADJUSTABLE GRID FOR MEDICAL THERAPY

[75] Inventors: James C. Chen, Bellevue, Wash.; Brent Wiscombe, Mesa, Ariz.

[73] Assignee: Light Sciences Limited Partnership, Issaquah, Wash.

[21] Appl. No.: 08/788,451

[22] Filed: Jan. 29, 1997

[51] Int. Cl.⁶ .................................................. A61N 5/00
[52] U.S. Cl. ............................ 607/88; 607/92; 607/115; 607/116
[58] Field of Search .................................. 606/14, 15, 16, 606/17, 10, 13, 2; 607/88, 89, 90, 92, 115, 116; 604/19, 20, 211

[56] References Cited

U.S. PATENT DOCUMENTS

| | | | |
|---|---|---|---|
| 4,761,047 | 8/1988 | Mori | 607/88 |
| 5,358,503 | 10/1994 | Bertwell et al. | 606/2 |
| 5,445,608 | 8/1995 | Chen et al. | 604/20 |
| 5,531,741 | 7/1996 | Barbacci | 606/15 |
| 5,800,478 | 9/1998 | Chen et al. | 606/14 |

*Primary Examiner*—Linda C. M. Dvorak
*Assistant Examiner*—R. Kearney
*Attorney, Agent, or Firm*—Ronald M. Anderson

[57] ABSTRACT

Flexible probes are arranged to achieve a desired light distribution pattern for administering light therapy at a treatment site in a patient's body. The flexible probes (20, 20', 92) each include a flexible substrate on which are mounted light emitting devices (30) in spaced-apart array. An optically transparent, biocompatible envelope (36) encloses the flexible substrate and components mounted thereon. In one embodiment, a link (44) couples a pair of the flexible probes together in parallel alignment for insertion at the treatment site. Thereafter, the probes are moved relative to each other within the link to achieve the desired light distribution pattern. In another embodiment, the flexible probes include flexible leaders (70, 72) attached to their distal ends, which terminate in suture tabs (74) that can be affixed to tissue adjacent the treatment site. The flexible probes are inserted into the treatment site generally aligned in a compact bundle and then are arrayed in a grid and spaced apart using links (82) to secure them at points where the flexible probes cross each other transversely. A further embodiment includes a strip (90) having a longitudinal slot (96), that opens into a channel (98) for receiving balls (94) formed on the distal ends of the flexible probes. The strip maintains the flexible probes in a spaced-apart array. Finally, another embodiment includes a flexible sheet (100) on which the flexible probes are mounted using sutures (108) or staples (102) after the sheet and flexible probes have been introduced to the treatment site.

29 Claims, 6 Drawing Sheets

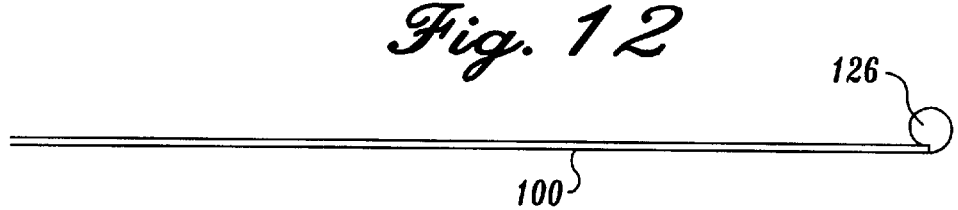
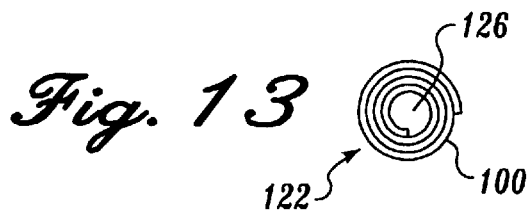
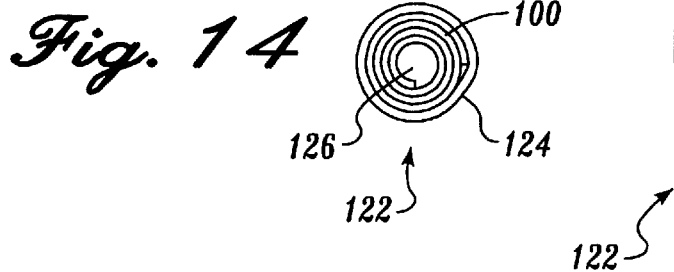
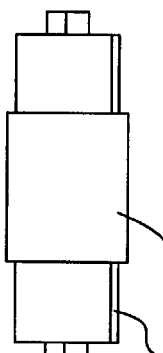
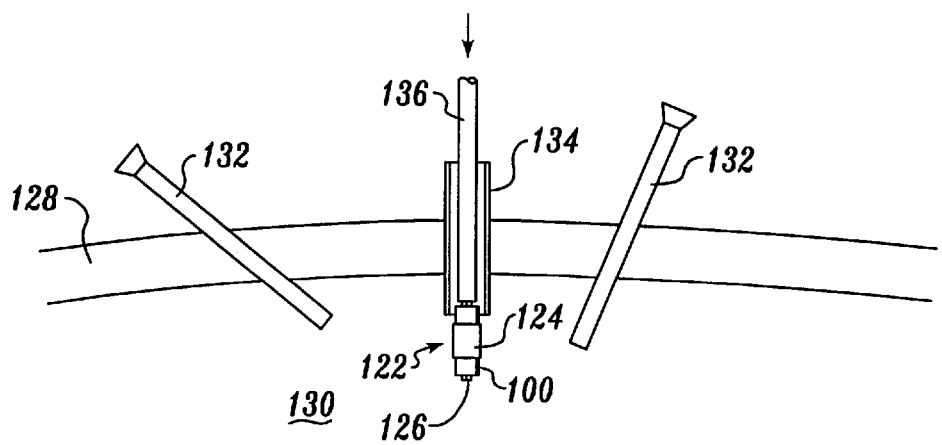

FLEXIBLE AND ADJUSTABLE GRID FOR MEDICAL THERAPY

FIELD OF THE INVENTION

The present invention generally relates to apparatus and a method for administering medical treatment at an internal treatment site within a patient, and more specifically, to apparatus and a method for locating a probe comprising an array of light sources at the internal treatment site to administer light therapy.

BACKGROUND OF THE INVENTION

Using a treatment referred to as photodynamic therapy (PDT), light can be used to destroy abnormal tissue in tumors and pathogenic organisms. Before administering PDT, an appropriate photoreactive agent is infused into the tissue at a treatment site or is applied to the organisms intended to be destroyed; the abnormal tissue or organisms absorb this agent to a much greater extent than surrounding normal tissue. Photoreactive agents have a characteristic light absorption waveband and react when exposed to light within that waveband by releasing free radicals and other chemicals. When a light source producing light having the absorption waveband of the photoreactive agent is directed at the treatment site, the abnormal tissue or disease organisms at the treatment site are destroyed by the chemicals produced by the photoreactive agent.

Typically, an external laser light source is used to administer PDT to a treatment site on the skin of a patient or at an internal treatment site that is surgically exposed. Alternatively, the light from the source may be conveyed to an internal treatment site such as a tumor through one or more optical fibers. Commonly assigned U.S. Pat. No. 5,445,608 discloses several different embodiments for providing PDT using transcutaneously implantable light source probes that include a plurality of relatively low intensity light sources, such as light emitting diodes (LEDs). It has been shown that relatively low intensity light administered for an extended period of time can be even more effective in PDT than high intensity light administered for a short period of time. Thus, the light source probes disclosed in the above-referenced patent are intended to be implanted and left in place at an internal treatment site to effect PDT over an extended time.

A commonly assigned U.S. patent application, Ser. No. 08/613,390, entitled "Flexible Microcircuits for Internal Light Therapy," filed on Mar. 7, 1996, discloses a number of flexible probes, each of which include a flexible substrate on which are disposed conductive traces electrically connected to leads through which electrical current is conveyed from a power source (implanted or external). A plurality of light sources are connected to the conductive traces and are mounted on the flexible substrate. A transparent, biocompatible polymer envelope encloses the flexible circuit and light sources, providing protection for the components as the flexible probe is advanced within the patient's body. This reference teaches that a flexible probe can readily be bent, folded, or rolled, thereby enabling the probe to pass through a guide tube, an incision, a catheter, or a lumen of relatively small diameter, to facilitate disposition of the probe at an internal treatment site. Once inserted at the internal treatment site, a folded or rolled flexible probe can be unfolded or unrolled to supply light for PDT or to implement other types of medical treatment. One of the embodiments disclosed in this reference is a flexible grid on which the plurality of light sources are disposed in a spaced-apart array. The reference teaches that the flexible grid can be conformed to a treatment site, e.g., wrapped around a tumor or a blood vessel. However, the reference does not disclose any means for shifting the light sources relative to the flexible substrate of the grid or for modifying the distribution of the light sources relative to the probe and its disposition at the treatment site. Clearly, it would be desirable to provide a mechanism enabling the configuration of light sources in an array to be adjusted, to optimize the pattern in which light is delivered to the treatment site. For example, many tumors have an irregular surface and are of varying thickness. A greater light intensity irradiating the thicker portion of the tumor relative to that irradiating the thinner portion would be required for optimum results. Thus, to treat such tumors, it would be preferable to configure a plurality of light sources at the treatment site, so that light is delivered to the tumor in a non-uniform distribution, with relatively more light being delivered to the thicker portions of the tumor than to the thinner portions. Furthermore, treatment sites having irregular surfaces could more effectively be treated with an array in which the position of the light source probes is adjustable at the treatment site than with an array in which the light sources or probes are in a fixed position.

Unless a treatment site is surgically exposed, configuring light sources after a probe has been implanted so as to irradiate a specific treatment site with light in a non-uniform distribution, would likely be done endoscopically. A flexible substrate grid on which light sources are mounted in fixed positions, as disclosed in the second reference discussed above, does not permit the configuration of light sources or probes to be altered once the grid is located at the treatment site within the patient's body. No currently available implantable array or probe provides the required flexibility in configuration. Accordingly, a different type of flexible array is needed that enables the location of light sources or probes comprising an array to be altered after the array is implanted inside a patient's body.

SUMMARY OF THE INVENTION

Apparatus for administering a light therapy to an internal treatment site to achieve a desired light distribution are provided in accord with the present invention. The apparatus includes a plurality of elongate probes, each elongate probe having a light source that emits light for effecting the light therapy. A power supply is coupled to the light source in each elongate probe to provide an electrical current for energizing the light source. Means are also included for coupling the plurality of elongate probes together at the internal treatment site. Thus, the elongate probes can be configured in a pattern that irradiates the treatment site with light having the desired light distribution.

In one embodiment, the means for coupling comprise a strip that includes a groove extending along a longitudinal axis of the strip. The groove has a cross-sectional shape that is adapted to receive and engage ends of the plurality of elongate probes to enable the plurality of elongate probes to be configured at the treatment site in the pattern. The ends of the elongate probes are preferably shaped to slide within the groove formed in the strip. A width of an opening into the groove is smaller than an interior portion thereof, and the ends of the elongate probes having a rounded knob shape that is larger in cross section than bodies of the elongate probes. The knob shaped ends of the elongate probes snap (or slide) through the opening into the groove of the strip so that the ends of the elongate probes engage the groove in the strip.

When configured in a pattern, for some of the embodiments, at least one of the plurality of elongate probes extends generally transverse to at least another of the plurality of elongate probes. In one of these embodiments, the means for coupling comprise a flexible leader that extends from at least one end of a portion of the plurality of elongate probes, to a common tab. The tab is adapted to connect to tissue adjacent the treatment site to secure the plurality of elongate probes in the pattern. A power lead extends from an end of each of the elongate probes opposite the end from which the flexible leader extends. The power leads that extend from the portion of the elongate probes that are connected to the common tab are coupled together at a common point. Similarly, power leads extending from a remainder of the elongate probes are coupled together at a different common point. Also, in these embodiments, the means for coupling comprise a clip for fastening together the elongate probes that are transverse to each other, at points where the elongate probes cross each other.

In another embodiment, the means for coupling comprise a sheet of material to which the plurality of elongate probes are fastened when positioned at the treatment site in the pattern. The sheet has a surface that substantially reflects the light emitted by the light source to increase the light incident on the treatment site.

In yet another embodiment, the means for coupling connect at least two of the elongate probes together so that said elongate probes are generally parallel.

An end of one of the two elongate probes extends substantially beyond the end of the other elongate probe.

In one embodiment, the means for coupling comprise loops that attach pairs of the elongate probes together. The loops enable the plurality of elongate probes to be configured in a bundle in which the elongate probes are generally parallel to each other, for transcutaneous insertion into the patient's body and placement at the treatment site. Subsequently, selected elongate probes in the bundle can be rotated so that they are generally transverse to the other elongate probes.

Generally, the means for coupling enable the plurality of elongate probes to be distributed in the desired pattern by adjustment of the spacing between adjacent elongate probes at the treatment site.

The light source preferably comprises a plurality of light emitting devices disposed in a spaced-apart array along a longitudinal axis of each elongate probe. The plurality of light emitting devices can be either light emitting diodes, vertical cavity surface emitting lasers (VCSELs), laser diodes, filament bulbs, or electroluminescent strips. Preferably, the elongate probes are flexible, and each elongate probe includes a plurality of flexible conductive traces on which the light source is mounted. The flexible conductive traces are coupled electrically to the power supply to energize the light source. In addition, the light source on each of the plurality of elongate probes is preferably enclosed within a biocompatible envelope that is optically transparent, at least on a side adjacent the light source.

Another aspect of the present invention is directed to a method for deploying a plurality of implantable light sources at an internal treatment site within a patient's body, where the plurality of light sources are deployed so as to achieve a desired light distribution over the internal treatment site to administer a light therapy. The method comprises steps that are generally consistent with the functions of the elements of the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 12 is a side elevational view of a partially rolled flexible support sheet;

FIG. 13 is an end view of a rolled flexible support sheet;

FIG. 14 is an end view of the rolled flexible support sheet and a retainer ring;

FIG. 15 is a plan view of the rolled flexible support sheet and retainer of FIG. 14;

FIG. 16 is a side elevational view illustrating the rolled support sheet being inserted into a patient's body through a laparoscopic guide tube that extends through a tissue layer;

DESCRIPTION OF THE PREFERRED EMBODIMENT

Figure 1:
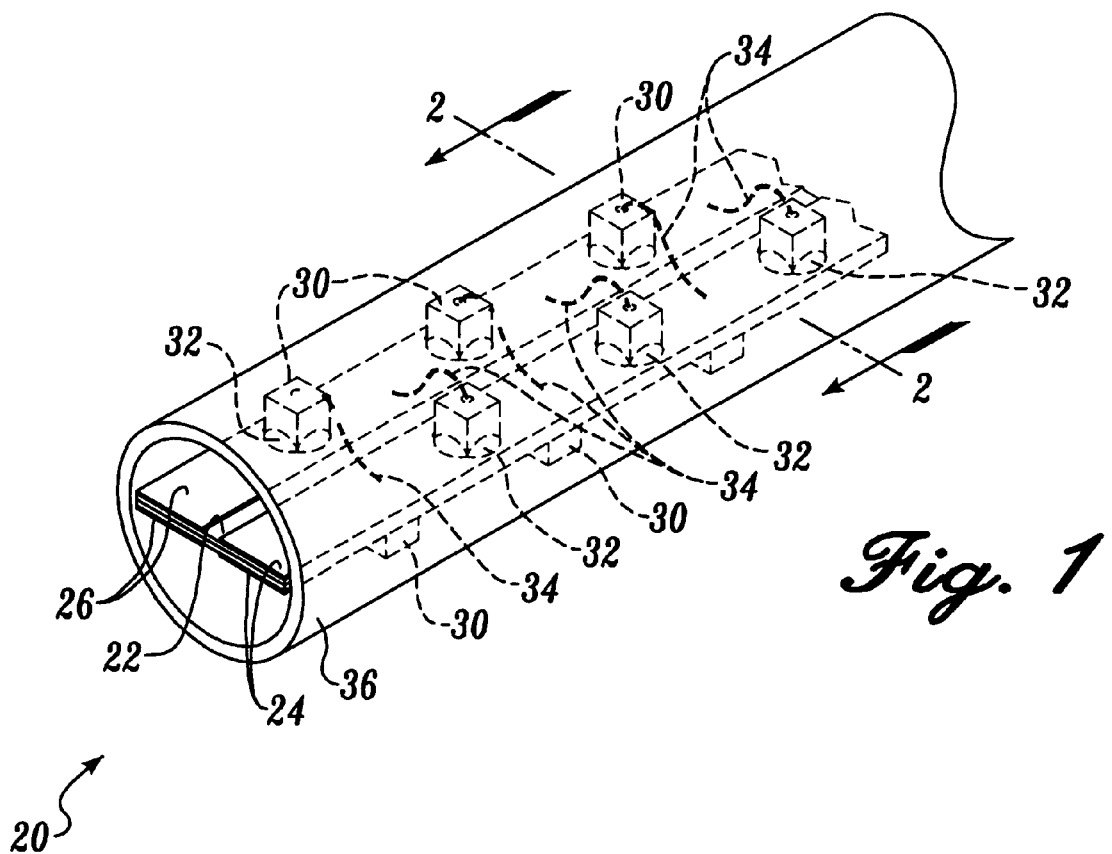
FIG. 1 is a cut-away isometric view of a portion of a flexible probe that is used in preferred embodiments of the present invention.

In the present invention, a plurality of elongate flexible probes 20 are introduced to a treatment site within a patient's body and then deployed in a configuration that provides a medical therapy, such as PDT, to the site, in a desired pattern. A portion of one of the flexible elongate probes is illustrated in FIG. 1. As shown in FIG. 1, flexible probe 20 includes a flexible substrate 22 that comprises a polymer plastic having relatively high dielectric strength or electrical insulating properties. On one side of substrate 22 are disposed parallel conductive traces 24 and 26, which extend in alignment with a longitudinal axis of the flexible substrate (and of the flexible probe). Conductive traces 24 and 26 are adapted to couple to a power supply (not shown) through electrical leads (also not shown in FIG. 1). The power supply can be either internal and spaced apart from the flexible probe or may be external to the patient's body. However, in the event that flexible probe 20 is left implanted within the patient's body for an extended period of time, it is generally undesirable for leads from the flexible probe to pass through the patient's skin, due to the risk of infection. Accordingly, it is generally preferable to provide an internal power source that is coupled through electromagnetic induction or by other means, to an outside source of power. It is also contemplated that the power source for the flexible probe may include a storage battery that is periodically recharged. However, these aspects of the use of flexible probe 20 are not particularly pertinent to the present invention and need not be further discussed herein.

Figure 2:
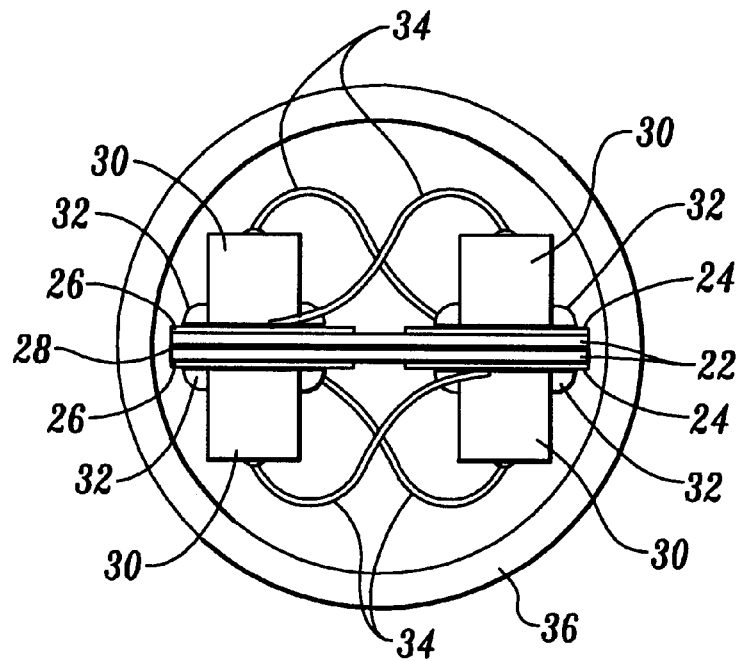
FIG. 2 is a cross-sectional view of the flexible probe of FIG. 1, taken along section lines 2—2.

As illustrated in greater detail in FIG. 2, a plurality of light emitting devices 30 are mounted on conductive traces 24 and 26 at spaced-apart intervals along their length. In the preferred embodiment, light emitting devices 30 comprise light emitting diodes (LEDs). It is also contemplated that different electronic devices used for a medical therapy can be included within flexible probe 20, either in place of or in addition to light emitting devices 30.

A terminal on one end of light emitting devices 30 is electrically connected to the conductive trace on which the device is mounted by a conductive adhesive/solder 32. The terminal on the opposite end of the light emitting device is electrically coupled to the other conductive trace through a fly wire 34 that is attached to the terminal and the conductive trace in a similar fashion. Since the flexible substrate 22 discussed above only has light emitting devices mounted on one surface, it may be preferable to include a second flexible substrate 22 on which light emitting devices are also mounted in the same manner. As shown in FIGS. 1 and 2, the second flexible substrate is adherently attached to the first flexible substrate using an appropriate adhesive layer 28, so that one flexible substrate is coupled back-to-back with the other flexible substrate, one on top and one on the bottom. Conductive traces 24 and 26 on the lower flexible substrate can be coupled in parallel to the power source with those on the upper flexible substrate, or can be independently coupled to the power source and independently controlled, as desired. Of course, only a single flexible substrate can be provided within flexible probe 20 if light therapy is only required to be directed to one side of the probe.

Surrounding the flexible substrates that are attached back-to-back and the light emitting devices mounted thereon is a cylindrical flexible envelope 36. To transmit light emitted from the light emitting devices to the adjacent treatment site, in the preferred embodiment of the present invention, flexible envelope 36 is optically transparent. Further, flexible envelope 36 is fabricated from a biocompatible material, such as a polymer plastic so that flexible probe 20 can be left implanted within a patient's body for an extended period of time without any undesired effects on the body. To protect the light emitting devices, flexible substrates 22, and other components within the flexible probe, flexible envelope 36 is sealed at both ends, and the electrical leads coupled to the conductive traces extend through the flexible envelope for connection to the power source.

Figure 3:
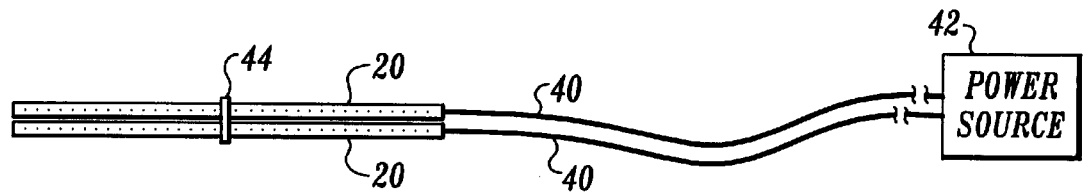
FIG. 3 is a plan view of two generally aligned flexible probes configured for insertion into a patient's body.

FIGS. 3–6 illustrate several different configurations for two flexible probes 20. In a configuration 38, which is shown in FIG. 3, the two flexible probes are shown generally aligned in a side-by-side relationship, with electrical leads 40 extending to a power source 42. A circular link 44 is fitted around the two flexible probes and is positioned generally at a center, along their longitudinal length. In configuration 38, flexible probes 20 are readily inserted into a patient's body through an opening that is excised transcutaneously, or alternatively, through a natural body orifice, such as the mouth or rectum. It will be evident that configuration 38 minimizes the cross-sectional size of the flexible probes, enabling them to be more readily inserted through a relatively small opening. Since flexible probes 20 are free to bend without causing damage to the circuitry contained therein, they can be readily manipulated to change their shape while being advanced to a treatment site within a patient's body. For example, it is likely that such probes may be moved along natural body passages, or between organs or other anatomical features within the body in which cross-sectional space is limited. The flexibility of these devices enables them to be advanced to treatment sites that might be impossible or extremely difficult to reach using a rigid probe.

Figure 4:
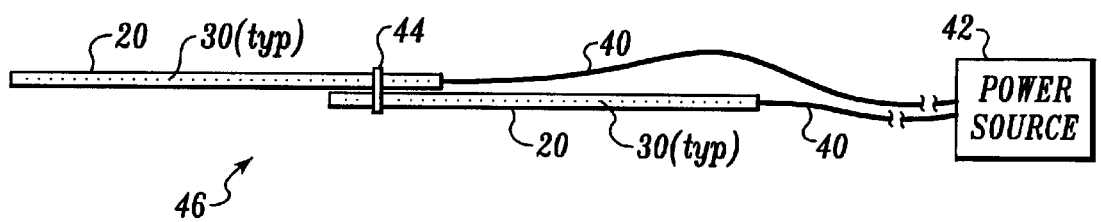
FIG. 4 is a plan view of the two flexible probes of FIG. 3, coupled together and configured for use at a treatment site.

FIG. 4 illustrates how flexible probes 20, once introduced into the patient's body in configuration 38, can be deployed in a configuration 46 to achieve a desired light distribution pattern or other distribution pattern desirable for a particular medical therapy administered by the flexible probes. To change from configuration 38 to configuration 46, the longitudinal disposition of two flexible probes is changed. For example, they are moved in opposite directions relative to their longitudinal axis by sliding them within link 44. Link 44 keeps the flexible probes coupled together while the probes are inserted into the treatment site and after their configuration is altered. It will be evident that when shifted into configuration 46, the overall length at which light emitted by light emitting devices 30 is incident on any adjacent treatment site is increased, thereby enabling the two flexible probes to provide light therapy to a substantially longer treatment site than is possible with only one flexible probe 20, or with two flexible probes when the probes are in configuration 38.

Figure 5:
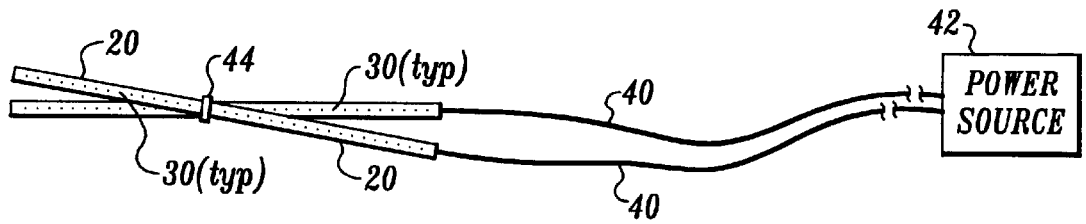
FIG. 5 is a plan view of the two flexible probes of FIG. 4, in a different configuration.

In FIG. 5, a configuration 48 is illustrated in which one of the flexible probes of configuration 38 has been rotated through an acute angle within link 44, relative to the other flexible probe. After the two flexible probes are introduced to the treatment site in configuration 38, they are simply pivoted about a point where link 44 is disposed to achieve configuration 48. Configuration 48 enables two flexible probes 20 to provide light therapy to an increased area at the treatment site, since the ends of the two flexible probes are spread apart from each other.

Figure 6:
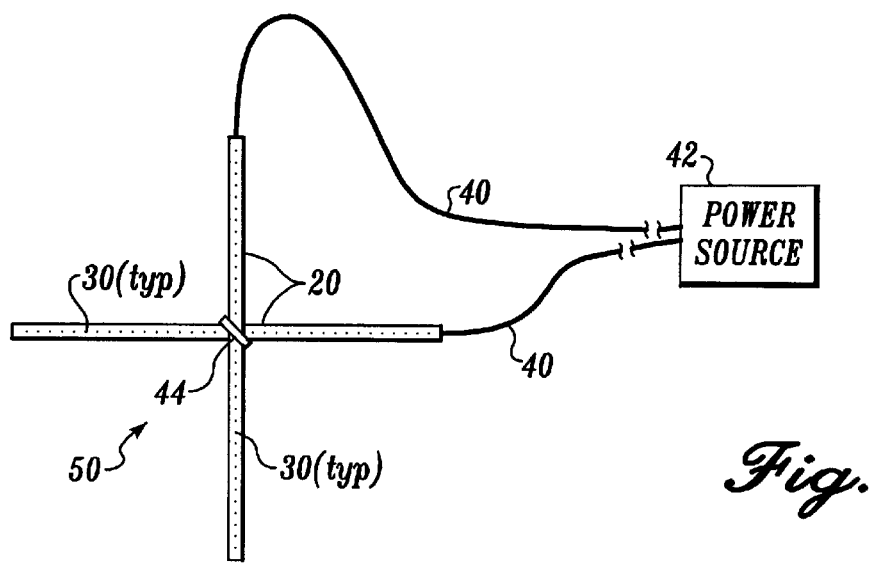
FIG. 6 is a plan view of the two flexible probes of FIG. 4, in yet another configuration.

FIG. 6 illustrates a configuration 50, which is similar to configuration 48, except that in configuration 50, the two flexible probes are pivoted through a greater angle so that they are substantially transverse to each other. This configuration again expands the total area over which light emitted by the light emitting devices within the flexible probes is incident, enabling the light therapy to cover a substantially greater area than would be possible for the flexible probes in configuration 38. It will be apparent that link 44 is sized sufficiently large to enable the two flexible probes to pivot through approximately a 90° angle while maintaining the flexible probes in intimate association with each other as they are inserted in the body in configuration 38. Further, it should be noted that virtually any angle between the probes up to approximately 90° can be achieved simply by pivoting one flexible probe relative to the other, as desired. Once the desired configuration is achieved, it is also contemplated that sutures or staples (not shown) can be applied to the probes or to electrical leads 40 to secure the flexible probes in the desired configuration.

Figure 8:
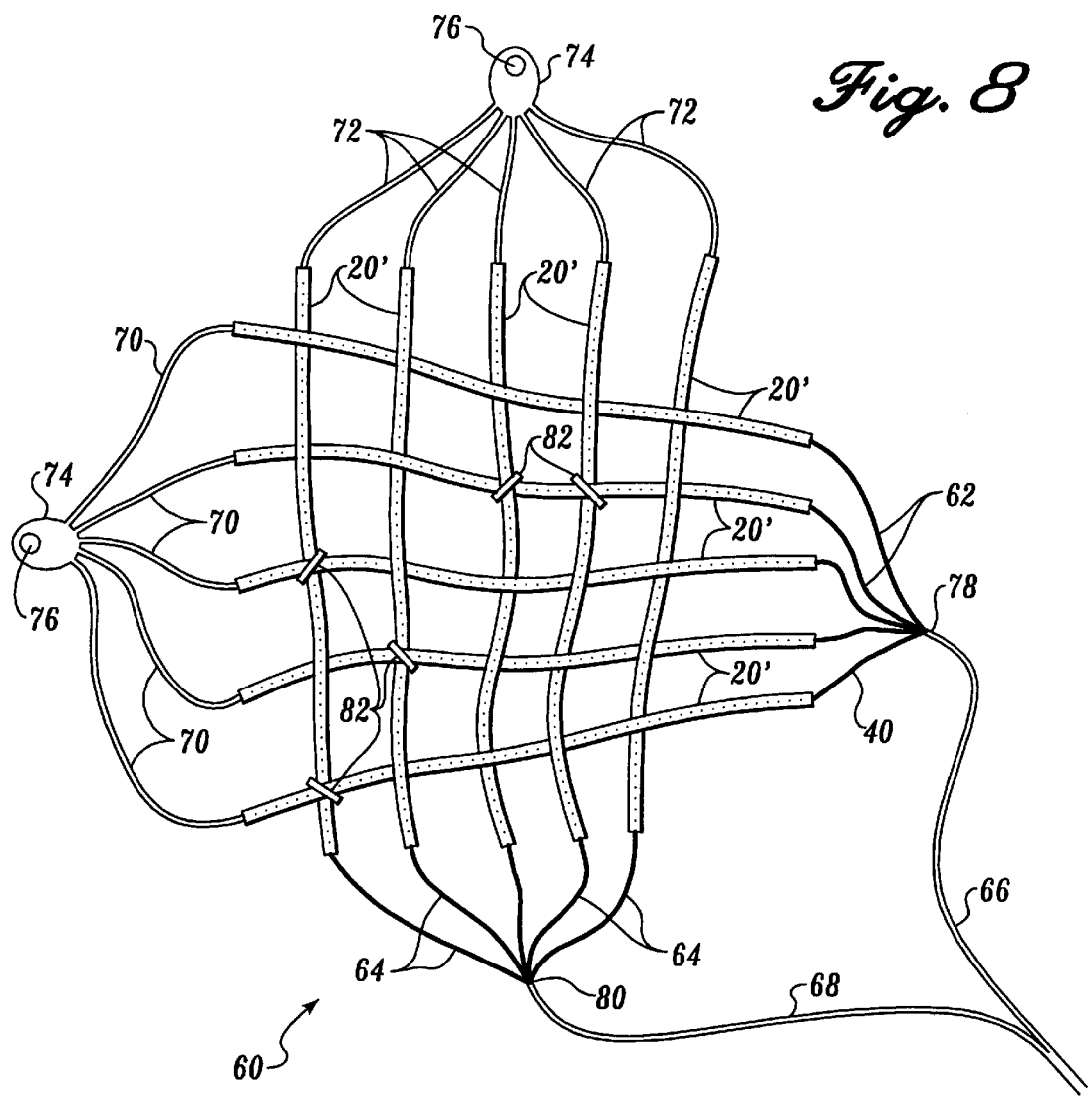
FIG. 8 is a plan view of the plurality of flexible probes, deployed in an array in which some of the probes are transverse to others of the probes.
Figure 7:
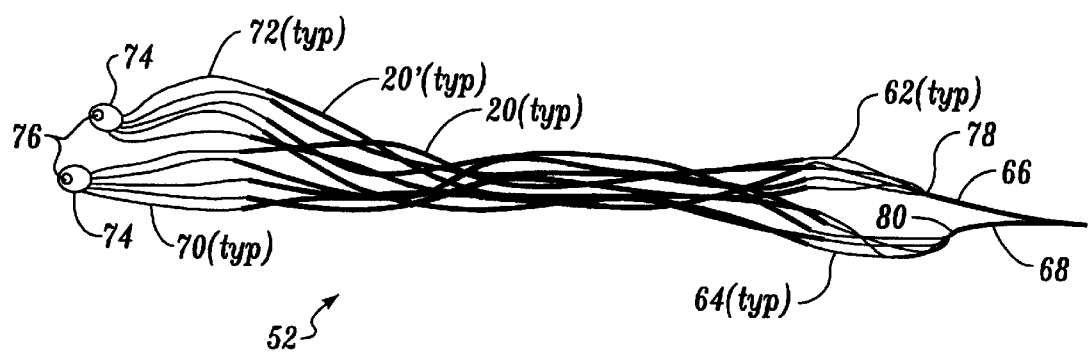
FIG. 7 is a plan view of a plurality of flexible probes, configured for insertion into a patient's body.

FIGS. 7 and 8 illustrate another embodiment of the present invention in which a plurality of flexible probes 20 and 20' grouped in a bundled array are passed into the body through a transcutaneous incision or natural body opening and then spread apart to cover a substantially larger area in order to administer a medical therapy to a treatment site within the patient's body Referring first to FIG. 7, the plurality of flexible probes are introduced into the body in a configuration 52 in which flexible probes 20 and 20' are generally loosely aligned in parallel with each other so that the bundle of flexible probes can be inserted through a relatively small diameter opening. In this embodiment, leads 62 extend from a proximal end of flexible probes 20 and are bound together at a node 78, forming a lead 66. Similarly, electrical leads 64 extend from a proximal end of each of flexible probes 20' and are bound together at a node 80, forming a lead 68. While not shown in FIGS. 7 and 8, the electrical leads in leads 66 and 68 are coupled to a power source, which is used to provide electrical current to energize light emitting devices 30, which are disposed within flexible probes 20 and 20'. At the opposite or distal ends of flexible probes 20 and 20' are respectively disposed flexible leaders 70 and 72; the flexible leaders comprise filaments of nylon or other suitable biocompatible polymeric material. Flexible leaders 70 are joined and terminate distally in a suture tab 74 in which is formed an orifice 76. Similarly, flexible leaders 72 are also joined together and terminate in another suture tab 74 that includes an orifice 76.

After flexible probes 20 and 20' are introduced into the patient's body in the generally aligned and bundled configuration, flexible leaders 70 and 72, and leads 62 and 64 are manipulated to spread the flexible probes apart and to arrange flexible probes 20' so that they are generally transverse to flexible probes 20. The result is a configuration 60, as shown in FIG. 8, in which the flexible probes are arranged in a grid. Once the flexible probes have been spread apart and distributed to achieve configuration 60, sutures or staples are applied through orifice 76 in each of the two suture tabs to fix the flexible probes in position relative to adjacent tissue. In addition, links 82 are optionally added to the array of flexible probes at any point where one flexible probe 20 crosses one of flexible probes 20' It is also contemplated that links 82 can be applied to the plurality of flexible probes before they are inserted into a patient's body in configuration 52. In the latter case, links 82 would be sufficiently large in their internal diameter to enable flexible probes 20 and 20' to be rotated through approximately a 90° angle, to achieve the grid array configuration after the flexible probes are introduced to the treatment site in the bundled and generally aligned configuration. Links 82 secure the flexible probes in place in configuration 60 and can be used to keep the probes in a bundle in configuration 52. Additional links 82 that cross the flexible probes in an "x" configuration (not shown) can be added for greater stability.

Although not shown, it is also contemplated that additional sutures can be applied to attach leads 62 and 64 in spaced-apart array to adjacent underlying tissue within the patient's body, using conventional endoscopic techniques. Since the relative position of each flexible probe 20 and 20' and the spacing between adjacent generally parallel flexible probes is readily adjusted, it is possible to position adjacent flexible probes relatively closer together in areas where the tissue mass being treated is relatively thicker than in other areas where it is relatively thinner. In this manner, the light distribution pattern at the treatment site can be optimized to achieve the most efficient therapy Furthermore, since flexible probes 20 and 20' are easily flexed into various curved shapes along their longitudinal axes, the flexible probes comprising the grid array of configuration 60 can be readily adjusted and manipulated to accommodate different shapes of the treatment site and to provide varying light intensity to different areas at the treatment site.

Figure 9:
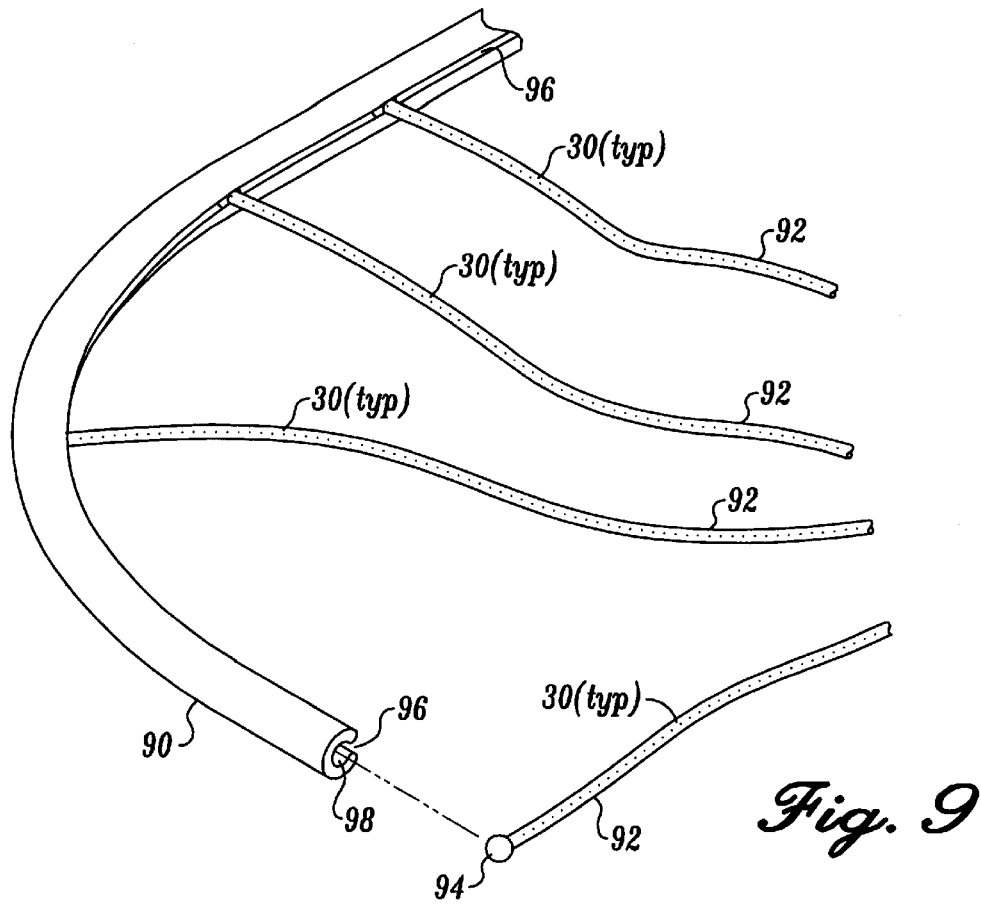
FIG. 9 is an isometric view of a supporting strip and a plurality of flexible probes engaged in a groove within the supporting strip.

Referring now to FIG. 9, a further embodiment of the present invention is illustrated wherein flexible probes 92 are introduced into the body, either singularly or in a compact bundle in which a plurality of the flexible probes are generally aligned. After the flexible probes are introduced to a treatment site, they are configured to achieve a desired light distribution pattern. Flexible probes 92 are generally identical in their internal construction to flexible probes 20 and 20' except that they include a ball 94 at their distal end. Although not shown, electrical leads are coupled to the proximal ends of flexible probes 92 as discussed above in connection with flexible probes 20.

To facilitate positioning flexible probes 92 into a desired configuration, a strip 90 is also inserted into the patient's body, and at the treatment site is arranged to hold the distal ends of the flexible probes in a spaced-apart array selected to provide the desired light distribution pattern. Strip 90 includes a slot 96 that opens into an internal channel 98, which extends the length of strip 90. Channel 98 has a generally circular cross-sectional shape, with a diameter generally equal to that of balls 94 on the distal ends of flexible probes 92. Accordingly, the ball-shaped ends on the flexible probes can be slipped into channel 98 from either end of the strip, so that the bodies of the flexible probes extend through slot 96. The flexible probes can then be slid along channel 98 to achieve a desired position and arranged in spaced-apart array to achieve the desired light distribution pattern.

It is also contemplated that rather than sliding balls 94 along channel 98, the balls can simply be forced into the channel through slot 96. Strip 90 comprises a biocompatible material, such as an appropriate plastic polymer, having elastomeric properties that accommodate forcing balls 94 through slot 96. It should also be noted that the proximal ends of flexible probes 92 can be arranged and maintained in a desired location by using sutures or staples to affix the electrical leads extending therefrom to adjacent tissue. It is also contemplated that a grid of flexible probes 92 can be produced using a plurality of strips 90 arranged to hold some of the flexible probes introduced to the treatment site in a position that is generally transverse to others of the flexible probes at the treatment site.

Figure 10:
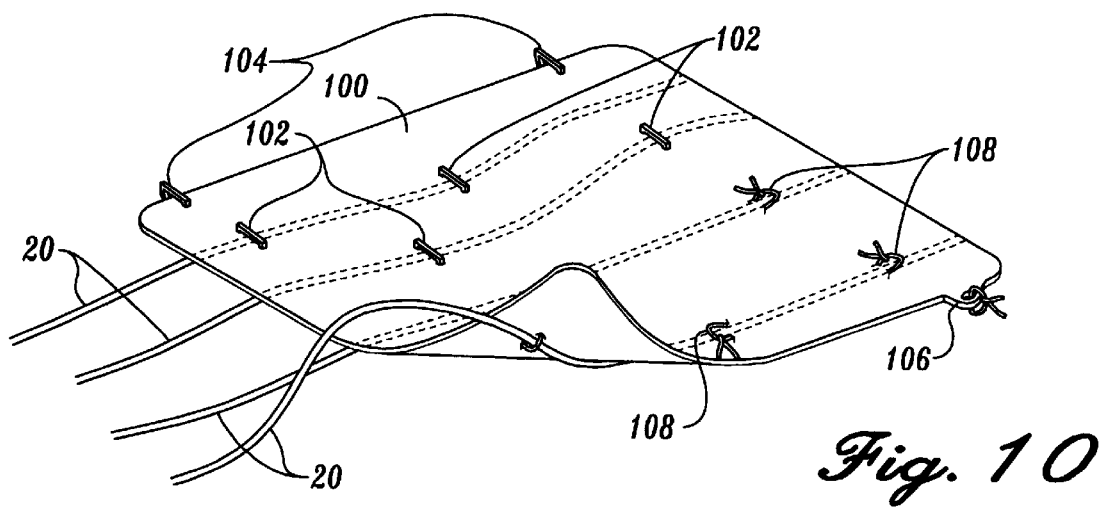
FIG. 10 is a flexible support sheet to which are attached a plurality of flexible probes.

Referring now to FIG. 10, another embodiment of the present invention is shown. In this embodiment, a plurality of flexible probes 20 are attached to a flexible sheet 100. The flexible probes 20 attached to the flexible sheet in this example are generally in parallel alignment with each other. However, it is also contemplated that the flexible probes may be secured to flexible sheet 100 so that some of the flexible probes are transverse to others at any desired angle. To secure the flexible probes to flexible sheet 100, staples 102 can be used, or alternatively, sutures 108 can be passed through the flexible sheet and around the exterior of the flexible probes, thereby securing them in place. As a further alternative, a biocompatible adhesive can be used to secure flexible probes to the flexible sheet. Similarly, staples 104 can be inserted through the periphery of flexible sheet 100 and into adjacent tissue to secure the flexible sheet with the attached flexible probes at the treatment site. Alternatively (or in addition), sutures 108 can be applied through a tab 106 on the periphery of flexible sheet 100, thereby securing it to adjacent tissue at the treatment site.

Figure 11:
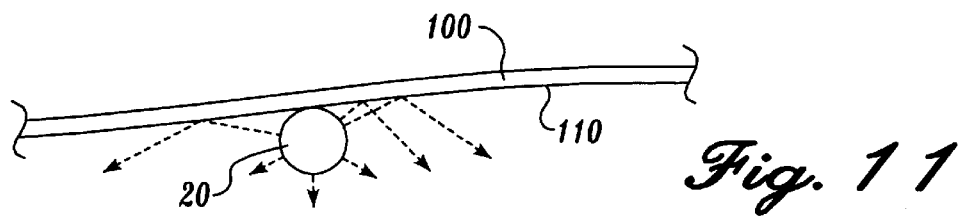
FIG. 11 is a side elevational view of a portion of the support sheet of FIG. 10 and one of the flexible probes.

FIG. 11 indicates that a surface 110 against which flexible probes 20 are mounted on flexible sheet 100 has light reflective properties. Since flexible sheet 100 can be fabricated from a suitable biocompatible plastic polymer, a color can be selected for the flexible sheet having a relatively high light reflectance value, or a highly light reflective coating can be applied to flexible sheet 100. As a result, light emitted by light emitting devices 30 within flexible probes 20 is reflected toward the treatment site, increasing the total illumination on the treatment site adjacent to the surface on which the flexible probes are mounted.

FIGS. 12 through 18 illustrate how flexible sheet 100 is inserted inside a patient's body using a laparoscopic procedure. In FIG. 12, flexible sheet 100 is shown before it is initially rolled into concentric cylindrical layers. To facilitate rolling the flexible sheet, a cylinder template 126 is preferably used. After flexible sheet 100 has been formed into a roll 122 as shown in FIG. 13, a sleeve 124 is slid over its outer surface, as shown in FIG. 14, preventing the rolled flexible sheet from unrolling. A push rod 136 is used to insert the rolled flexible sheet retained by sleeve 124 through a guide tube 134, as shown in FIG. 16. The guide tube is surgically positioned so that it extends through a tissue layer 128 to access an internal treatment site 130. Also illustrated in this Figure are two laparoscopic tubes 132, both of which are inserted through tissue layer 128 at opposite sides of guide tube 134 so that their distal ends are disposed adjacent treatment site 130. Flexible sheet 100 is deployed and unrolled to serve as a support for the flexible probes, which are introduced to the site and attached to the flexible sheet, as discussed above.

Figure 17:
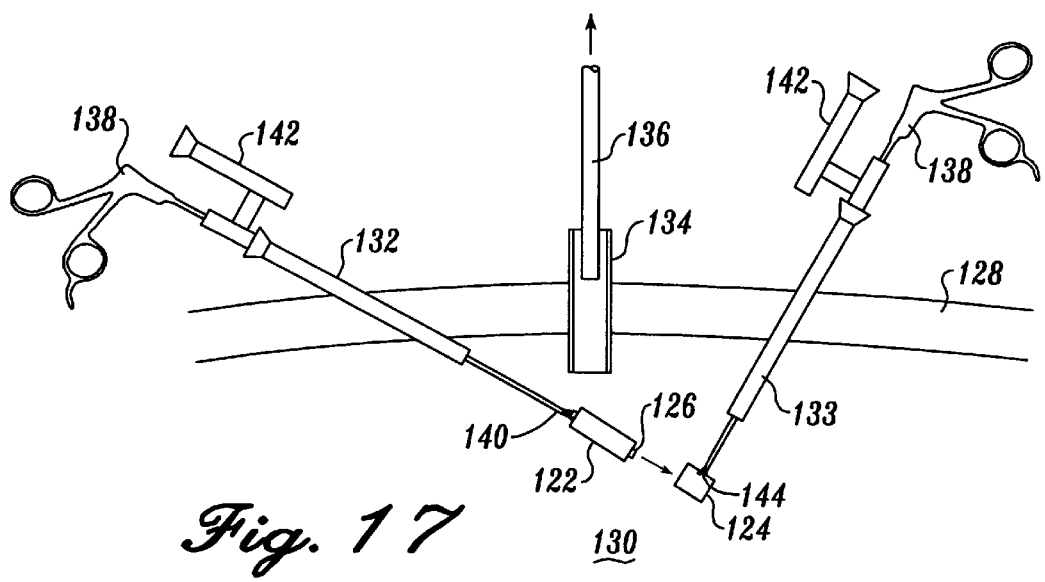
FIG. 17 is a side elevational view showing laparoscopic forceps being used to remove the retainer from the rolled flexible sheet.
Figure 18:
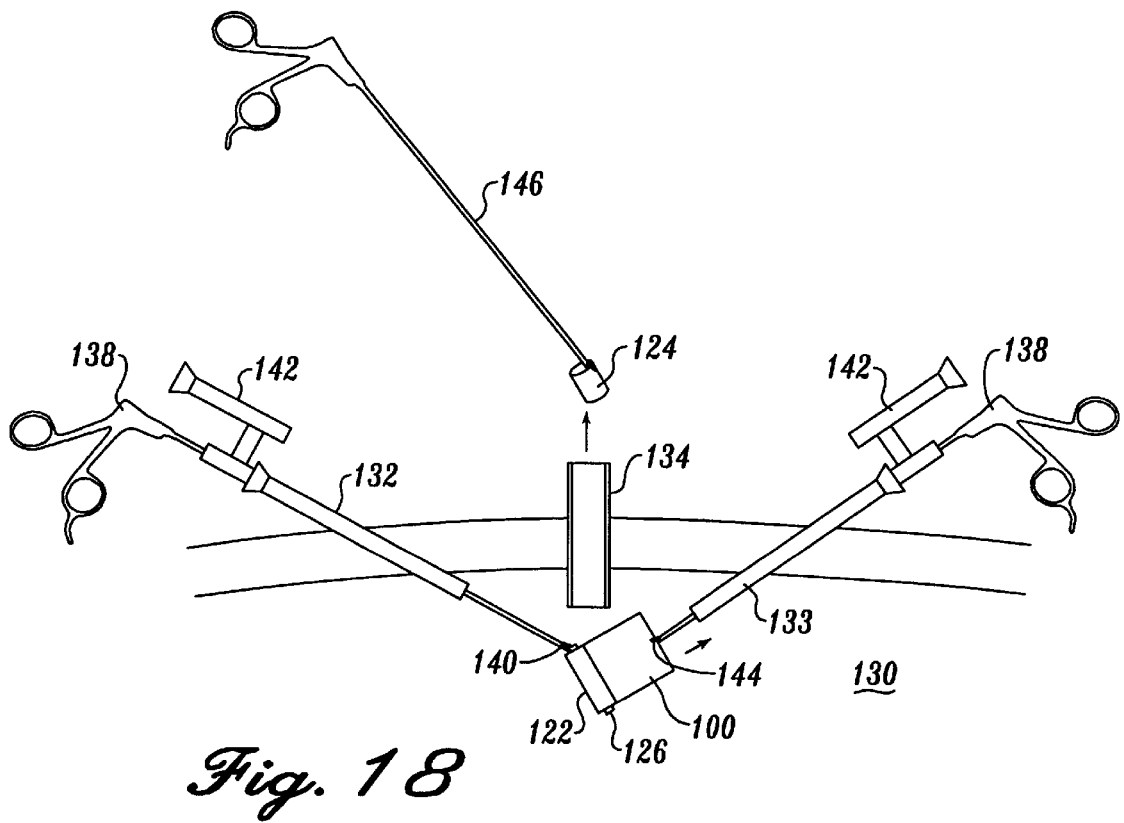
FIG. 18 is a side elevational view showing laparoscopic forceps being used to unroll the flexible support sheet to enable it to be used for supporting flexible probes at an internal treatment site.

In FIG. 17, laparoscopes 138 are inserted through laparoscopic tubes 132 to enable sleeve 124 to be withdrawn from rolled flexible sheet 122. Push rod 136 is then extracted through guide tube 134. Eye pieces 142, which are provided on each of laparoscopes 13S, enable the operator to manipulate rolled flexible substrate 122 and sleeve 124 during this procedure. Next, as shown in FIG. 18, forceps 146 are inserted through guide tube 134 and employed to grasp sleeve 124, withdrawing it from treatment site 130. In addition, laparoscopes 138 are used to unroll flexible sheet 122 at treatment site 130. In this operation, template 126 is grasped by laparoscope 138 using forceps tip 140, which is disposed at its distal end, while flexible sheet 100 is grasped by forceps tip 144 on the other laparoscope. While not shown in the Figures, forceps 146 are then used to withdraw template 126 through guide tube 134.

Flexible sheet 100 is thus unrolled at the treatment site and flexible probes are inserted through guide tube 134 into the treatment site, where they are mounted to flexible sheet 100 as discussed above. Using this technique, the flexible probes can be mounted on flexible sheet 100 to achieve any desired light distribution pattern on the treatment site. The flexible sheet with the flexible probes mounted thereon is then fixed in place at the treatment site by attaching it to adjacent tissue Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for administering a light therapy to an internal treatment site to achieve a desired light distribution over the internal treatment site, comprising:

(a) a plurality of elongate probes, each elongate probe including a light source that emits light for effecting the light therapy, and each elongate probe adapted to be moveably positionable relative to each other;

(b) electrically conductive leads for coupling the plurality of elongate probes to a power supply that provides an electrical current for energizing the light source in each elongate probe; and (c) means for coupling the plurality of elongate probes together at the internal treatment site in a modifiable configuration that irradiates the treatment site with light having a desired light distribution pattern.

2. The apparatus of claim 1, wherein the means for coupling comprise a strip having a longitudinal axis and a groove extending along the longitudinal axis of the strip, said groove having a cross-sectional shape that is adapted to receive and engage ends of the plurality of elongate probes to enable the plurality of elongate probes to be configured at the treatment site in said pattern.

3. The apparatus of claim 2, wherein the ends of the elongate probes are shaped to engage and slide within the groove formed in the strip.

4. The apparatus of claim 2, wherein a width of an opening into the groove is smaller than an interior portion thereof, the ends of the elongate probes having a rounded knob shape that is larger in cross section than bodies of the elongate probes, said knob shaped end of an elongate probe snapping through said opening into the groove of the strip so that the end of the elongate probe is engaged in the groove.

5. The apparatus of claim 1, wherein when configured in said desired light distribution pattern, at least one of the plurality of elongate probes extends generally transversely to at least another of the plurality of elongate probes.

6. The apparatus of claim 5, wherein the means for coupling comprise a flexible leader that extends from at least one end of a portion of the plurality of elongate probes, to a common tab for said portion of the elongate probes, said tab being adapted to connect to tissue adjacent to the treatment site to hold the plurality of elongate probes at the treatment site and secure said plurality of elongate probes in said pattern.

7. The apparatus of claim 5, wherein the means for coupling comprise a clip for fastening together the elongate probes that are transverse to each other, at any point where said elongate probes cross each other.

8. The apparatus of claim 1, wherein an electrically conductive lead extends from ends of a first group of the elongate probes, said electrically conductive leads being coupled together at a first common point, and electrically conductive leads extending from ends of a second group of the elongate probes being coupled together at a second common point.

9. The apparatus of claim 1, wherein the means for coupling comprise a sheet of material to which the plurality of elongate probes are fastened when positioned at the treatment site and arranged in said pattern.

10. The apparatus of claim 9, wherein the sheet has a surface that substantially reflects the light emitted by the light source toward the treatment site to increase the light incident on the treatment site.

11. The apparatus of claim 1, wherein the means for coupling connect at least two of the elongate probes together so that said elongate probes are generally parallel.

12. The apparatus of claim 11, wherein the means for coupling enable an end of one of said two elongate probes to extend substantially beyond an end of another of said two elongate probes.

13. The apparatus of claim 1, wherein the means for coupling comprise loops that attach pairs of the elongate probes together, said loops enabling the plurality of elongate probes to be configured in a bundle in which the plurality of elongate probes are generally aligned side-by-side for transcutaneous insertion into the patient's body and placement at the treatment site, said loops subsequently enabling selected elongate probes to be rotated so that they are generally transverse to others of said plurality of elongate probes.

14. The apparatus of claim 1, wherein the means for coupling enable the plurality of elongate probes to be configured to achieve said desired light distribution pattern by adjustment of a spacing between adjacent elongate probes at the treatment site.

15. The apparatus of claim 1, wherein the light source comprises a plurality of light emitting devices disposed in a spaced-apart array along a longitudinal axis of each elongate probe.

16. The apparatus of claim 15, wherein a type of light emitting device used for said light source comprises at least one of:
 (a) a light emitting diode;
 (b) a vertical cavity surface emitting laser;
 (c) a laser diode;
 (d) an ionized gas light source;
 (e) a filament bulb; and
 of an electroluminescent strip.

17. The apparatus of claim 1, wherein the elongate probes are flexible, each elongate probe including a plurality of flexible conductors coupled to the light source, said flexible conductors being electrically coupled to the electrically conductive leads.

18. The apparatus of claim 1, wherein the light source on each of the plurality of elongate probes is enclosed within a biocompatible envelope that is optically transparent on at least a side disposed adjacent to the light source.

19. Apparatus for delivering a medical treatment to an internal treatment site, comprising:
 (a) a plurality of elongate probes, each elongate probe including a plurality of electrical conductors;
 (b) a plurality of electrical leads electrically connected to the plurality of electrical conductors, said plurality of leads being adapted to connect to a power source;
 (c) a plurality of electronic devices disposed on the elongate probes and electrically connected to the plurality of electrical conductors, said plurality of electrical conductors conveying an electrical current from the power source to energize the plurality of electronic devices, when the plurality of leads are connected to the power source, said plurality of electronic devices being adapted to administer the medical treatment to the treatment site when thus energized by the electrical current; and
 (d) at least one link for coupling the plurality of elongate probes together so that the plurality of probes are movable relative to each other and thus enabling a configuration of the plurality of elongate probes to be modified after the plurality of elongate probes are disposed at the treatment site, by moving the plurality of elongate probes relative to each other.

20. The apparatus of claim 19, wherein each of the plurality of elongate probes comprises a flexible substrate on which the plurality of electrical conductors are disposed.

21. The apparatus of claim 19, wherein each of the plurality of elongate probes further includes a flexible, biocompatible polymer envelope, with said plurality of leads extending from said envelope.

22. The apparatus of claim 19, wherein the plurality of electronic devices comprise a plurality of light sources for use in administering a light therapy.

23. The apparatus of claim 19, wherein said at least one link comprises one of a clip and a suture.

24. The apparatus of claim 19, wherein the plurality of elongate probes are selectively configurable as a collapsed grid in which the plurality of elongate probes are generally aligned with each other, and as an expanded grid in which at least one of the plurality of elongate probes extends in a direction substantially transverse to at least another of the plurality of elongate probes.

25. The apparatus of claim 19, further comprising a flexible leader having a proximal end connected to at least one of the plurality of elongate probes, and a distal end connected to a tab that is adapted for attachment to the patient's body, to fix the tab, the flexible leader, and said at least one of the plurality of elongate probes at the internal treatment site.

26. The apparatus of claim 25, where in at least two of the plurality of elongate probes are connected to flexible leaders having distal ends connected to a common tab.

27. The apparatus of claim 19, wherein said at least one link couples at least two of the plurality of elongate probes together and permits at least one of said at least two elongate probes to slide generally along a longitudinal axis of another of said at least two elongate probes.

28. The apparatus of claim 19, wherein a plurality of links couple different pairs of the plurality of elongate probes together, enabling one elongate probe of each pair to move relative to another elongate probe of the pair.

29. The apparatus of claim 28, comprising additional links that are added after the plurality of elongate probes has been disposed in a desired configuration at the treatment site, said additional links affixing the plurality of elongate probes in said desired configuration.

* * * * *